US00PP21832P2

(12) United States Plant Patent
Meijer

(10) Patent No.: US PP21,832 P2
(45) Date of Patent: Mar. 29, 2011

(54) ***HELLEBORUS* PLANT NAMED 'CINDERELLA'**

(50) Latin Name: ***Helleborus orientalis* hybrid**
Varietal Denomination: Cinderella

(75) Inventor: Henk Meijer, Ridderkerk (NL)

(73) Assignee: Gootjes-Allplant B.V., Heerhugowaard (NL)

( * ) Notice: Subject to any disclaimer, the term of this patent is extended or adjusted under 35 U.S.C. 154(b) by 0 days.

(21) Appl. No.: 12/655,763

(22) Filed: Jan. 6, 2010

(51) Int. Cl.
*A01H 5/00* (2006.01)

(52) U.S. Cl. ..... Plt./439

(58) Field of Classification Search ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'Cinderella', characterized by its upright to outwardly arching plant habit; freely flowering habit; semi-double flowers that are greenish white in color with greyed purple-colored spots; and good garden performance.

2 Drawing Sheets

Botanical designation: *Helleborus orientalis* hybrid.

Cultivar denomination: 'CINDERELLA'.

BACKGROUND OF THE INVENTION

The present invention relates to a new and distinct cultivar of *Helleborus* plant, botanically known as *Helleborus orientalis* hybrid, and hereinafter referred to by the name 'Cinderella'.

The new *Helleborus* plant is a product of a planned breeding program in Buitenpost, The Netherlands. The objective of the breeding program was to create new double-type *Helleborus* cultivars with attractive leaf and flower coloration.

The new *Helleborus* plant originated from a cross-pollination conducted by the Inventor in Buitenpost, The Netherlands in February, 2003 of two unnamed proprietary seedling selections of *Helleborus orientalis* hybrid, not patented. The new *Helleborus* plant was discovered and selected by the Inventor as a single flowering plant from within the progeny of the stated cross-pollination grown in a controlled greenhouse environment in Buitenpost, The Netherlands in March, 2005.

Asexual reproduction of the new *Helleborus* plant by tissue culture in a controlled greenhouse environment in Enkhuizen, The Netherlands since March, 2006, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cinderella'. These characteristics in combination distinguish 'Cinderella' as a new and distinct cultivar of *Helleborus:*

1. Upright to outwardly arching plant habit.
2. Freely flowering habit.

3. Semi-double flowers that are greenish white in color with greyed purple-colored spots.
4. Good garden performance.

Compared to plants of the parent selections, plants of the new *Helleborus* are more uniform and more freely flowering.

Plants of the new *Helleborus* can be compared to plants of *Helleborus orientalis* hybrid 'HLR 160', disclosed in an U.S. Plant Pat. No. 21,504. Plants of the new *Helleborus* differ primarily from plants of 'HLR 160' in flower form as plants of 'HLR 160' have single-type flowers.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'Cinderella' grown in a container.

The photograph at the top of the second sheet is a close-up view of a typical flower of 'Cinderella'.

The photograph at the bottom of the second sheet is a close-up view of typical leaves of 'Cinderella'.

DETAILED BOTANICAL DESCRIPTION

The aforementioned photographs and following observations, measurements and values describe plants grown in Zevenbergen, The Netherlands in 1.5-liter containers during the winter in a glass-covered greenhouse and under conditions which closely approximate commercial *Helleborus* production. During the production of the plants, day temperatures ranged from 5° C. to 20° C. and night temperatures ranged from 1° C. to 15° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus orientalis* hybrid 'Cinderella'.

Parentage:

*Female, or seed, parent.*—Unnamed proprietary seedling selection of *Helleborus orientalis* hybrid, not patented.

*Male, or pollen, parent.*—Unnamed proprietary seedling selection of *Helleborus orientalis* hybrid, not patented.

Propagation:

*Type.*—By tissue culture.

*Time to initiate roots.*—About ten days at 20° C.

*Time to produce a rooted young plant.*—About two months at 12° C. to 20° C.

*Root description.*—Thick, fibrous; light brown in color.

*Rooting habit.*—Low branching; moderately dense.

Plant description:

*Plant form and growth habit.*—*Herbaceous* perennial; upright to outwardly arching plant habit; moderately vigorous growth habit.

*Plant height.*—About 40 cm.

*Plant diameter* (*area of spread*).—About 39.4 cm.

Foliage description:

*Arrangement.*—Palmately compound with five leaflets per leaf.

*Leaf length.*—About 12.9 cm.

*Leaf width.*—About 17.1 cm.

*Leaflet length.*—About 8.2 cm.

*Leaflet width.*—About 4.3 cm.

*Leaf shape.*—Palmate; orbicular in outline.

*Leaflet shape.*—Obovate; lowest leaflets cleft.

*Leaflet apex.*—Acute.

*Leaflet base.*—Attenuate.

*Leaflet margin.*—Sharply serrate.

*Leaflet texture, upper and lower surfaces.*—Smooth, glabrous; leathery.

*Leaflet venation pattern.*—Pinnate.

*Leaflet color.*—Developing leaves, upper surface: Close to 143A. Developing leaves, lower surface: Between 143B and 144A. Fully developed leaves, upper surface: Close to N137A; venation, close to 144A to 144B. Fully developed leaves, lower surface: Close to 147B; venation, close to 143C.

*Petiole.*—Length: About 14.2 cm. Diameter: About 3 mm. Texture, upper and lower surfaces: Smooth, glabrous. Color, upper and lower surfaces: Close to 143A to 144B; towards the base, tinged with close to 183C.

Flower description:

*Flower shape and habit.*—Semi-double rotate flowers; freely flowering habit with about five flowers per terminal cluster; petals not observed.

*Fragrance.*—None detected.

*Natural flowering season.*—Plants flower during the late winter in The Netherlands; plants begin flowering about ten months after planting.

*Flower longevity on the plant.*—About twelve days; flowers not persistent.

*Flower buds.*—Length: About 1.8 cm. Diameter: About 1.1 cm. Shape: Ovate. Color: Close to 157A; towards the base, close to 145A to 145B.

*Flowers.*—Diameter: About 5.7 cm. Depth (height): About 2.6 cm.

*Sepals.*—Arrangement: About five in a single whorl. Length: About 3.4 cm. Width: About 3.1 cm. Shape: Broadly ovate to orbicular. Apex: Rounded. Margin: Entire. Texture, upper and lower surfaces: Smooth, glabrous. Color: When opening, upper surface: Close to 157D; towards the base, close to 144C; spots, close to 187B to 187C. When opening, lower surface: Between 145D and 157A; towards the base, close to 144A to 144B. Fully opened, upper surface: Between NN155B and 157D; towards the base, close to 145B to 145C; spots, close to 187C. Fully opened, lower surface: Between 145D and 157A; towards the base, close to 144A to 144B.

*Sepaloids.*—Arrangement: About 17 in about two whorls. Length: About 3 cm. Width: About 1.6 cm. Shape: Rhomboidal. Apex: Acute. Margin: Entire. Texture, upper and lower surfaces: Smooth, glabrous. Color: When opening, upper surface: Close to 157D; towards the base, close to 144C; spots, close to 187B to 187C. When opening, lower surface: Between 145D and 157A; towards the base, close to 144A to 144B. Fully opened, upper surface: Between NN155C and 157D; towards the base, close to 145C to 145D; spots, close to 187C. Fully opened, lower surface: Between 145D and 157A; towards the base, close to 144A to 144B.

*Peduncles.*—Strength: Moderately strong. Length: About 31 cm. Diameter: About 6 mm. Aspect: About 10° from vertical. Texture: Smooth, glabrous. Color: Close to 144A slightly tinged with close to 176C to 176D.

*Pedicels.*—Strength: Moderately strong. Length: About 2.2 cm. Diameter: About 2.5 mm. Aspect: Mostly erect. Texture: Smooth, glabrous. Color: Close to 144C to 144D.

*Reproductive organs.*—Stamens: Quantity per flower: About 80. Filament length: About 1.1 cm. Filament color: Close to 155D. Anther shape: Reniform. Anther length: About 3 mm. Anther color: Close to 157B to 157C. Pollen amount: Scarce. Pollen color: Close to 155A to 155B. Pistils: Quantity per flower: About four. Pistil length: About 1.5 cm. Stigma shape: Club-shaped. Stigma color: Close to 157D. Style length: About 1.4 cm. Style color: Close to 145A; towards the base, close to 182B. Ovary color: Close to 150B.

*Seeds/fruits.*—Seed and fruit development have not been observed.

Garden performance: Plants of the new *Helleborus* have been observed to have good garden performance and to tolerate rain and wind. Plants of the new *Helleborus* have been observed to tolerate high temperatures of about 35° C. and are hardy to USDA Hardiness Zone 5.

Pathogen/pest resistance: Plants of the new *Helleborus* have not been shown to be resistant to pathogens and pests common to *Helleborus*.

It is claimed:

1. A new and distinct *Helleborus* plant named 'Cinderella' as illustrated and described.

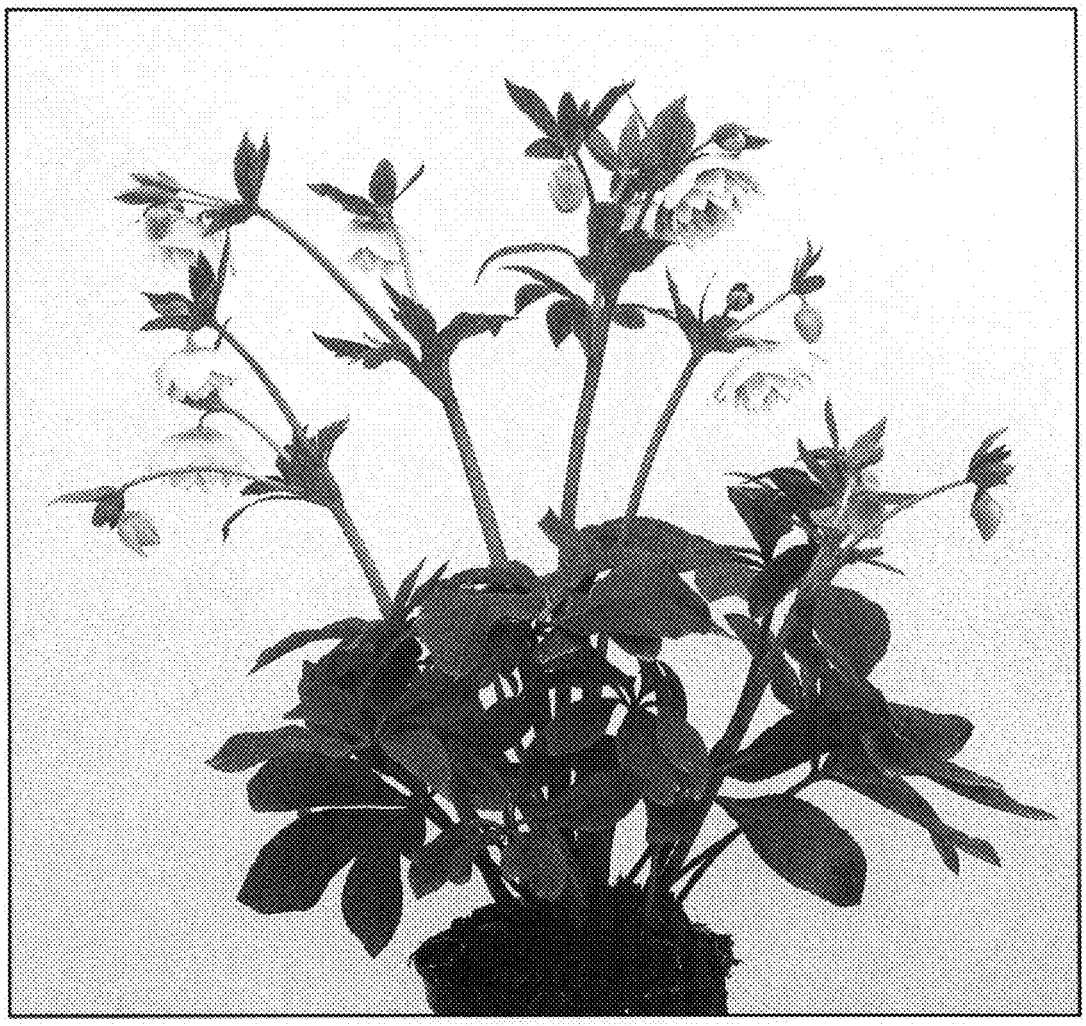

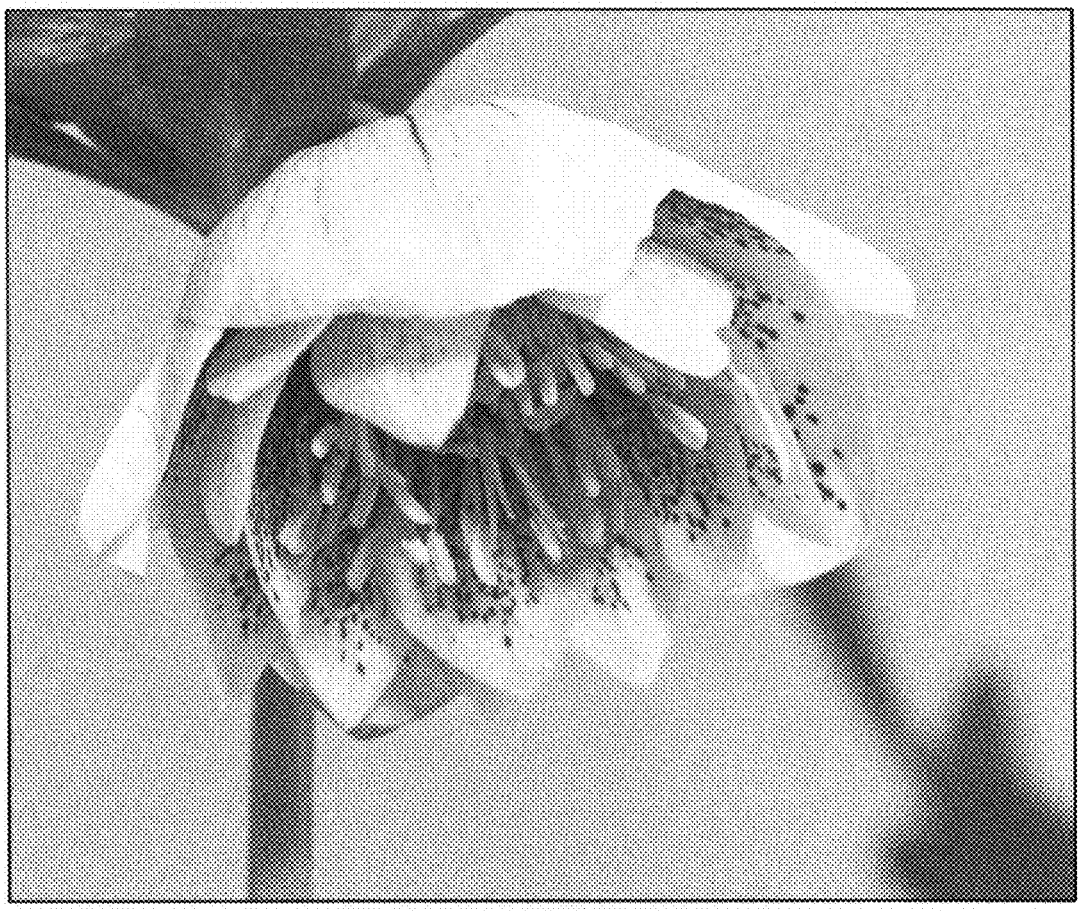
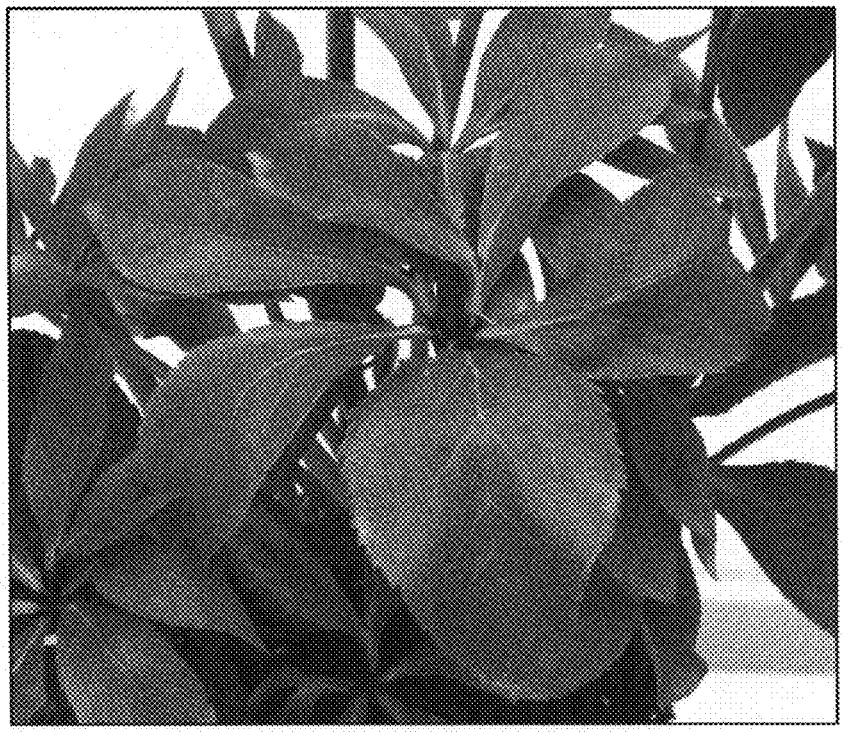

* * * * *